(12) United States Patent
Acker

(10) Patent No.: US 6,580,938 B1
(45) Date of Patent: Jun. 17, 2003

(54) IMAGE-GUIDED THORACIC THERAPY AND APPARATUS THEREFOR

(75) Inventor: David E. Acker, Setauket, NY (US)

(73) Assignee: Biosense, Inc., Setauket, NY (US)

( * ) Notice: Subject to any disclaimer, the term of this patent is extended or adjusted under 35 U.S.C. 154(b) by 578 days.

(21) Appl. No.: 09/030,241

(22) Filed: Feb. 25, 1998

Related U.S. Application Data

(60) Provisional application No. 60/038,497, filed on Feb. 25, 1997.

(51) Int. Cl.[7] .................................................. A61B 5/00
(52) U.S. Cl. ...................... 600/424; 600/427; 600/429
(58) Field of Search ................................ 600/411, 413, 600/424, 427, 428, 429, 529, 534; 128/899; 606/130

(56) References Cited

U.S. PATENT DOCUMENTS

| | | |
|---|---|---|
| 4,989,608 A | 2/1991 | Ratner |
| 5,316,024 A | 5/1994 | Hirschi et al. |
| 5,391,199 A | 2/1995 | Ben-Haim |
| 5,443,489 A | 8/1995 | Ben-Haim |
| 5,482,042 A | 1/1996 | Fujita |
| 5,558,091 A | 9/1996 | Acker et al. |
| 5,577,502 A | 11/1996 | Darrow et al. |
| 5,671,739 A | 9/1997 | Darrow et al. |
| 5,730,129 A | 3/1998 | Darrow et al. |
| 5,775,322 A | 7/1998 | Silverstein et al. |

FOREIGN PATENT DOCUMENTS

| | | |
|---|---|---|
| WO | WO 97/29709 | 8/1997 |

Primary Examiner—Ruth S. Smith
(74) Attorney, Agent, or Firm—Lerner, David, Littenberg, Krumholz & Mentlik, LLP

(57) ABSTRACT

A probe such as an endoscope equipped with a biopsy needle is guided to a target in or adjacent to the respiratory system. The position of the probe is monitored and a representation of the probe is superposed on a previously acquired image of the respiratory system and adjacent tissues. Artifacts caused by motion due to respiration are suppressed by monitoring the respiratory state of the patient and acquiring the probe position when the respiratory state of the patient is equal to the respiratory state of the patient during image capture.

3 Claims, 2 Drawing Sheets

IMAGE-GUIDED THORACIC THERAPY AND APPARATUS THEREFOR

CROSS REFERENCE TO RELATED APPLICATIONS

The present application claims benefit of United States Provisional Patent Application 60/038,497 filed on Feb. 25, 1997, the disclosure of which is incorporated by reference herein.

BACKGROUND OF THE INVENTION

The present invention relates to methods and apparatus for performing medical procedures in the thorax of a medical or veterinary patient.

Some common medical procedures require the ability to operate on a specific location in the thorax, including locations in the respiratory system, such as the lungs, bronchi and immediately surrounding tissues. For example, needle aspiration biopsies have been performed heretofore using an endoscope inserted through the trachea into a bronchus. The needle is advanced through the endoscope through the bronchial wall to sample tissue in a lymph node within the lung parenchyma near the exterior surface of the bronchus. The physician can monitor placement of the endoscope and the biopsy needle using the optical system of the endoscope. As the endoscope is advanced toward the area to be sampled, the physician can determine where the tip of the endoscope lies by observing features of the airway itself. However, it is difficult to place a biopsy needle within a particular lymph node using this approach. The physician cannot see the lymph nodes, which lie outside of the airway. Therefore, the physician can only position the endoscope tip and the biopsy needle at an approximate position, near the location of the lymph node to be biopsied. For this reason, there has been a significant need for improvement in the reliability of needle aspiration biopsies of the lymph nodes surrounding the respiratory tract. There have been similar needs for improvement in other biopsies procedures using a probe advanced into the body, such as a biopsy needle or biopsy forceps to sample tissues in the vicinity of the respiratory tract. There have been similar needs for improvement in other procedures where a probe is advanced into the tissues of the thorax for other purposes as, for example, to perform surgical procedures on these tissues or to administer drugs within these tissues.

Some procedures heretofore have used imaging during advancement of the probe to provide guidance. Thus, as the probe is advanced, the probe and the body are imaged using conventional imaging techniques such as fluoroscopy or magnetic resonance imaging. This allows the physician to observe the relationship between the position of the probe and the surrounding tissues. These procedures have the disadvantage that the imaging apparatus is occupied for the entire time required to perform the procedure. Moreover, the use of fluoroscopic or other x-ray based imaging modalities during the procedure exposes the physician and the patient to radiation.

As described, for example, in U.S. Pat. Nos. 5,558,091, 5,391,199; 5,443,489; and in PCT International Publication WO 96/05768, the disclosures of which are hereby incorporated by reference herein, the position, orientation or both of the distal end of a probe can be determined by using one or more field transducers such as a Hall effect or magnetoresistive device, coil or other antenna carried on the probe, typically at or adjacent the distal end of the probe. One or more additional field transducers are disposed outside the body in an external frame of reference. The field transducers preferably are arranged to detect or transmit non-ionizing fields or field components such as a magnetic field, electromagnetic radiation or acoustical energy such as ultrasonic vibration. By transmitting the field between the external field transducers and the field transducers on the probe, characteristics of field transmission between these devices can be determined. The position and/or orientation of the sensor in the external frame of reference can then be deduced from these transmission characteristics. Because the field transducer of the probe allows determination of the position of the probe, such transducer is also referred to as a "position sensor".

As described, for example, in the aforementioned U.S. Pat. No. 5,558,091, the frame of reference of the external field transducers can be registered with the frame of reference of imaging data such as magnetic resonance imaging data, computerized axial tomographic data, or conventional x-ray image data. The probe position and orientation data derived by field transmission can be displayed as a representation of the probe superimposed on an image of the patient's body. The physician can use this information to guide the probe to the desired location within the patient's body, and to monitor its orientation during treatment or measurement of the body structure. This arrangement greatly enhances the ability of the physician to navigate the distal end of the probe through bodily structures. Because it does not require acquisition of an optical image of the surrounding tissues for navigation purposes, it can be used with probes which are too small to accommodate optical elements, and can be used for navigation of the probe within solid or semisolid tissues. The transducer-based system also avoids the difficulties associated with navigation of a probe by continuous imaging of the probe and patient during the procedure. For example, it avoids exposure to ionizing radiation inherent in fluoroscopic systems.

Some additional problems are encountered in use of systems of this type for procedures in the thorax near the respiratory system. As the patient breathes, the positions, sizes and shapes of the thoracic organs change. Thus, if an image of the patient is acquired at one stage of the respiratory cycle, the image data does not accurately represent the patient during other stages. Therefore, if the position of the probe is detected while the patient is in one stage of the respiratory cycle, and this probe position data is combined with patient image data from another stage of the respiratory cycle to provide an image with a representation of the probe superposed thereon, the location of the probe relative to the surrounding organs will be depicted inaccurately.

As described in International Publication WO 97/29709, the disclosure of which is incorporated by reference herein, problems of this nature can be avoided by positioning a first probe, referred to as a "site probe" within the body of the patient at a location to be treated, and providing a further probe, referred to as an "instrument probe" for performing the medical procedure. The site probe is positioned within the body at the location to be treated as, for example, at a location to be biopsied. Using a location system such as the magnetic location systems discussed in the aforementioned patents, the locations of both probes are monitored during the medical procedure. Therefore, the distance and direction from the instrument probe to the site probe are known during the medical procedure, despite any motion caused by the patient's breathing. Using that directional and distance information, the physician can navigate the instrument probe to the site probe.

PCT Publication WO 97/29682 refers to systems for determining the "physiological motion" such as breathing motion or cardiac motion of a portion of the body in which a probe is situated. Using a device such as a belly strap to sense breathing motion, the system selects a "correct" image from a set of previously obtained images at each instant during the procedure, or interpolates between images. Thus, the displayed image always reflects the actual size and shape of the organs at the instant in question. Accordingly, the representation of the probe can be accurately superposed on the display image.

U.S. Pat. No. 5,577,502 discloses a system in which the position of the subject's chest is monitored by devices such as optical, ultrasound or mechanical tracking elements. Based on that positional tracking, the image used in a superposition system is distorted so as to provide a corrected image which changes as the subject breathes. The position of the probe can be superposed on the corrected image. Systems of this type require considerable computation to distort the reference image as the patient moves through various stages of the respiratory cycle. Moreover, additional equipment is required for tracking the position of the patient's chest. In an alternative approach also discussed in the '502 patent, a series of images is acquired at numerous stages of the respiratory cycle. As the patient moves through different stages of the respiratory cycle, different images are employed. This approach multiplies the task of acquiring and storing the image data. Moreover, this approach can only be used if a set of multiple images exists. For example, where the patient is subjected to a conventional diagnostic imaging procedure such as an MRI or CT imaging, a single set of image data representing the patient at only one stage of the respiratory cycle generally is acquired. The need for a biopsy or other procedure using a probe advanced into the patient may only be apparent after that image has been evaluated. To acquire a series of images, the patient must be subjected to further imaging procedures before the interventional procedure using the probe can begin.

Thus, despite these and other efforts in the art, further improvements in interventional procedures and apparatus for performing the same would be desirable.

SUMMARY OF THE INVENTION

One aspect of the present invention provides methods of performing medical procedures on thoracic tissues, and particularly on tissues of the respiratory system or tissues adjacent the respiratory system. A method according to this aspect of the present invention includes the steps of providing an image of the patient in an image frame of reference representing the patient at a selected respiratory state, such as in a selected stage of the normal respiratory cycle, and advancing a probe into the respiratory system of the patient by adjacent tissues. During the advancing step, the disposition of the probe is determined in a locating frame of reference when the patient is at the aforesaid selected respiratory state. The disposition of the probe desirably is detected by transmitting one or more non-ionizing fields to or from at least one probe field transducer on the probe and detecting one or more properties of the transmitted fields. The method further includes the step of transforming the image, the disposition of the probe in the locating frame of reference or both so as to place the image and the disposition of the probe into a common frame of reference. Typically, the transforming step is performed by transforming the disposition of the probe in the locating frame of reference into the image frame of reference. The method further includes the step of displaying the image of the patient with a representation of the probe superposed thereon, at a location corresponding to the disposition of the probe in the aforesaid common frame of reference.

Because the disposition of the probe used as the basis for the superposed representation is acquired at the same stage in the respiratory state as the image, the motion artifact or inaccuracy caused by motion due to the respiratory cycle is eliminated. Methods according to this aspect of the invention thus provide a solution to the motion artifact problem which does not require acquisition of multiple images for massive manipulation of the image data to distort an image. The system is compatible with standard images acquired for diagnostic purposes, which represent only one stage in the respiratory cycle.

The method preferably further includes the step of detecting when the patient is in the selected stage of the respiratory cycle by monitoring the position of a reference point on a patient which moves in respiration. Preferably, the system detects when the patient is in the selected respiratory state by determining whether the position of the reference point matches a selected position corresponding to the selected respiratory state within a preselected tolerance. For example, where the image was acquired at a particular stage of respiration, the system acquires the disposition of the probe during each breath, at the same stage of respiration. The method may further include the step of establishing a particular position of the reference point which corresponds to a selected stage of the respiratory cycle by monitoring the position of the reference point over a plurality of respiratory cycles and finding an extreme position of the reference point which recurs in each cycle using the data acquired by this monitoring procedure. For example, the selected stage of the respiratory cycle may be the minimum inspiration state, i.e., the state achieved at the end of exhalation during a normal breathing cycle. In this case, the system may select the position of the reference point at which the patient's front chest wall is closest to the patient's back. If the patient is lying in a supine position with his or her back on a table, the system may select the position where a reference point on the patient's front chest wall is closest to the table.

The step of monitoring the position of the reference point desirably includes the step of transmitting one or more non-ionizing fields to or from at least one reference field transducer on the reference point. Thus, the position of the reference point can be monitored using much of the same equipment and techniques as are used for monitoring the position of the probe.

Desirably, the system displays a perspective image of the tissues surrounding the probe as, for example, a perspective image of an airway and surrounding tissues with the probe superposed thereon. The image is displayed so that the position of the probe and the trajectory for moving the probe to engage a target location such as a lymph node is readily visible by viewing the displayed image. Typically, the step of advancing the probe is performed by advancing the probe through an airway as, for example, by passing the probe through the wall of the airway to sample tissue at a target location such as the lymph nodes outside of the airway. The probe may include an endoscope and a needle. The step of advancing the probe may be performed by advancing the endoscope until the endoscope is positioned at the wall of the airway adjacent the target location, and then advancing the needle through the wall of the airway.

During some portions of the probe-advancing step, the patient may be instructed to hold his or her breath at the prescribed respiratory state. Thus, while the patient holds the prescribed point in the respiratory state, the system will continually acquire new positions of the probe and will continually update the superposed representation of the probe on the image. If the patient momentarily deviates from the prescribed stage of the respiratory cycle, the system will stop generating new superposed positions of the probe representation on the image and preferably will provide a warning to the physician.

Further aspects of the present invention provide apparatus for monitoring the respiratory cycle of a medical patient. Apparatus according to this aspect of the invention desirably includes means for monitoring the position of a reference point on a patient which moves in the respiratory cycle and means for finding an extreme position of a reference point which recurs in each cycle based on the data acquired in the monitoring operation. The apparatus desirably further includes means for determining whether the position of the reference point matches such extreme position to within, a preselected tolerance. Apparatus according to this aspect of the present invention can be used in the aforementioned methods. Desirably, the means for monitoring the position of a reference point includes a reference field transducer adapted for mounting on the exterior of a patient's thorax at the reference point and one or more external field transducers defining a locating frame of reference. The apparatus desirably further includes sensing means for transmitting one or more non-ionizing fields between the external field transducers and the reference field transducer, detecting one or more properties of the transmitted fields and determining the position of the reference field transducer in the locating frame of reference from the so detected properties. The apparatus may further include a probe adapted for insertion into the respiratory system of a patient of the surrounding tissues, and at least one probe field transducer on the probe. The sensing means desirably is operative to transmit one or more non-ionizing field between the external field transducers and the probe field transducers, to detect one or more properties of these transmitted fields and to determine the position of the probe field transducer in the locating frame of reference from these properties. As discussed above in connection with the methods, apparatus in accordance with this aspect of the present invention can utilize the same position measuring devices as employed in determining the probe position to determine the respiratory cycle.

DETAILED DESCRIPTION OF THE PREFERRED EMBODIMENTS

Figure 1:
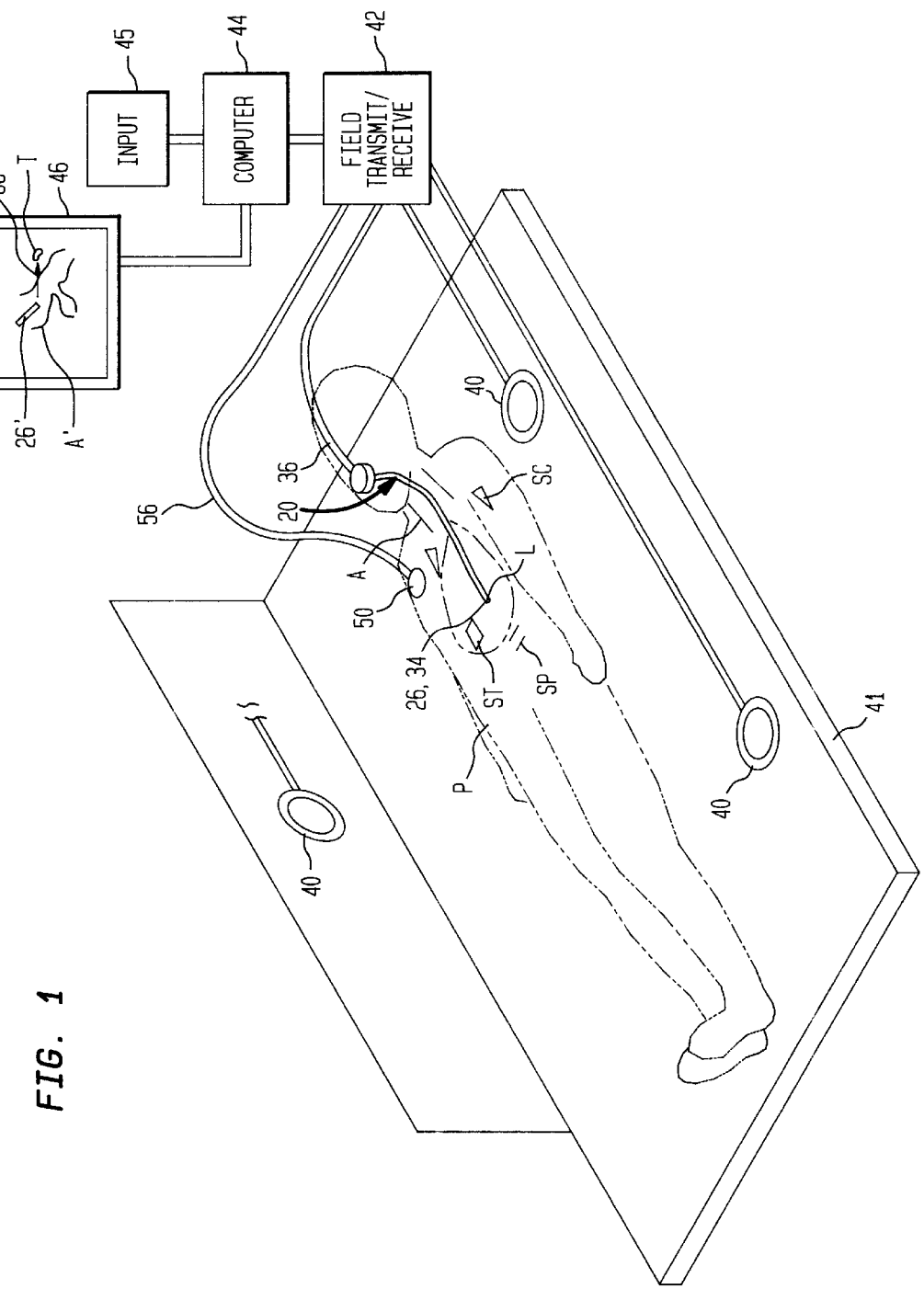
FIG. 1 is a diagrammatic perspective view depicting elements of apparatus in accordance with one embodiment of the invention in conjunction with a patient.
Figure 3:
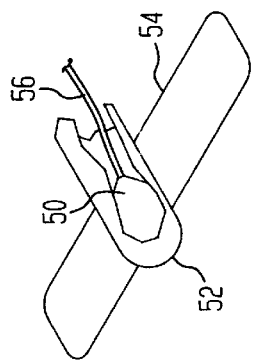
FIG. 3 is a diagrammatic perspective view showing further elements of the apparatus.

Apparatus according to one embodiment of the present invention includes a probe 20. The probe may incorporate essentially any device which can be inserted or advanced into the body to perform a medical procedure, such as treatment, measurement or observation. As used herein, the term "treatment" includes capturing samples of tissues or materials present within the body, and thus includes biopsies. The probe 20 desirably includes a conventional endoscope having a tubular body 22. Body 22 has a handle portion 24 affixed to a proximal end of the body and has a distal portion 26 remote from handle 24. Body 22 has a bore 28 extending longitudinally from its proximal end to its distal end and open to the outside through handle 24. Body 22 may incorporate a flexible section adjacent the distal end, so that the distal end 26 can be bent or pivoted relative to the remainder of the body. The endoscope may incorporate devices (not shown) for bending the distal end of the body so as to steer the device as it is advanced into the patient's anatomy. The endoscope may further include a fiber optic or television system (not shown) for visually observing the anatomical features of the patient at the distal end of the endoscope.

The probe further includes a conventional intrabody medical tool such as a biopsy needle 30 or other surgical tool operable from the proximal end or handle of the device. Merely by way of example, instead of a biopsy needle, the tool may be any conventional surgical tool of the type commonly used in endoscopic, arthroscopic, a laparoscopic surgical procedures; a biopsy forceps or other sampling device; a needle, catheter or other drug delivery device; a measuring instrument such as a thermometer or electrical potential measuring electrode; a device for applying therapeutic radiation; or any other device which can be used to treat, measure or observe structures within the body of a living subject. Needle 30 is arranged so that it can be advanced to an operative position 30' outside of the distal end of body 22. Needle 30 is arranged so that it can be manipulated and controlled from the proximal end or handle 24 of the body. Thus, the needle is connected to a manipulating handle 32 by conventional control elements or linkages. Other expedients for manipulating and controlling a tool at the distal end of body can be employed as, for example, electrical, electronic or optical control linkages. Alternatively, a tool can be mounted in fixed position on body 22 or formed integrally therewith as, for example, where body 22 is equipped with a cutting blade.

A probe field transducer or position sensor 34 is mounted in probe body 22 adjacent the distal end 26 thereof Transducer 34 may be a sensor arranged to detect magnetic or electromagnetic fields. For example, the sensor 34 may be a multiaxis, solid-state position sensor of the type disclosed in the aforementioned U.S. Pat. No. 5,558,091. Such a sensor incorporates a plurality of transducers sensitive to magnetic field components in mutually orthogonal directions. Other suitable position sensors include coils as disclosed in the aforementioned U.S. Pat. No. 5,391,199 and in PCT Application PCT/US95/01103, now published as PCT International Publication WO 96/05768, the disclosure of which is hereby incorporated herein by reference. Such coils may be provided as a single coil or as a plurality of orthogonal coils capable of detecting field components in orthogonal directions. Position sensor or field transducer 34 is connected to leads 36 which extend through bore 28 to and beyond the proximal end 24 of body 22.

The apparatus further includes a set of external field transducers or antennas 40 defining a locating frame of reference. For example, external field transducers 40 may be mounted to a patient-supporting bed 41. Antennas 40 are linked to a field transmitting and receiving device 42 and a computer 44, which in turn is linked to a display device such as a cathode ray tube 46. The computer is also provided with conventional input devices 45 such as a keyboard, trackball, mouse and the like. Computer 44, field transmitting and receiving device 42 and transducers 40 are arranged to cooperate with the probe field transducer 30 to determine the dispositions of the field transducer on the probe, and hence determine the disposition of the distal end of the probe in the locating frame of reference of the external field transducers or antennas 40. These elements of the apparatus can be as described in the aforementioned '091 or '199 patents. Other devices for detecting disposition of probes equipped with position sensors by transmission of non-ionizing fields are known in the art. As is known in the art, electromagnetic or magnetic fields can be transmitted between an antenna or field transducer mounted in an external frame of reference and a field transducer on a probe, and the disposition of the probe can be calculated from the characteristics of the fields detected by the transducer on the probe. Thus, the external field transducers or antennas 40 and the position sensor or probe field transducer 34 on the probe cooperatively define a plurality of transmitter-receiver pairs. Each such pair includes one transmitter and one receiver as elements of the pair. One element of each such pair is disposed on the probe and the other element of each such pair is disposed at a known disposition in the external frame of reference. Typically, at least one element of each transmitter-receiver pair is disposed at a different position or orientation than the corresponding element of the other pairs. By detecting the characteristics of field transmission between elements of the various pairs, the system can deduce information concerning the disposition of the probe in the external frame of reference. The disposition information can include the position of the probe, the orientation of the probe or both. Although the external field transducers 40 are illustrated as mounted to a rigid structure such as a patient bed, so that the external field transducers remain in fixed position relative to one another, this is not essential. As described in commonly assigned PCT Publication WO 97/29685, the disclosure of which is incorporated by reference herein, the external field transducers may be movable relative to one another. The computer system can determine the positions of the external field transducers by measuring the properties of fields transmitted between these transducers, or between the external field transducers and calibration transducers mounted to the individual external field transducers.

The apparatus further includes a reference field transducer 50 mounted in a protective housing 52 effective to protect field transducer 50 from physical damage when the field transducer is deployed at a position on the outside of a patient's body. Thus, the housing 52 and field transducer 50 can be mounted by any conventional expedient such as adhesive tape, bandages, sutures or the like at a selected point on the exterior of a patient. Optionally, housing 52 may be provided with features such as flat pads or wings 54, suture holes (not shown) or other physical features which further facilitate attachment to the exterior surface of the body. Reference field transducer 50 has essentially the same structure as probe field transducer 34 discussed above. Leads 56 connect the reference field transducer to the field transmitting and receiving device 42. The field transmitter and receiver 42 and computer 44 actuate external field transducers 40 and reference field transducer 50 to transmit and receive fields in the same manner as discussed above in connection with probe field transducer 34. Thus, the system determines the disposition of the reference field transducer in the locating frame of reference defined by external field transducers 40.

In a method according to one embodiment of the invention, a patient P is imaged using any conventional imaging modality such as computerized tomographic x-ray ("CAT" or "CT") imaging, magnetic resonance imaging or any other imaging method which is capable of depicting the internal organs of the body and, particularly, the respiratory system and surrounding tissues. The image is acquired while the patient is at a selected respiratory state. The selected respiratory state may be a state which is not part of the patient's normal respiratory cycle, such as a forced inhalation or forced exhalation. Preferably, the selected respiratory state is a stage of the patient's normal respiratory cycle. Preferably, the image is acquired while the patient is at the so-called "minimum inhalation" stage. This stage is the stage during normal breathing where the patient has exhaled the normal, tidal volume of air. The patient may be instructed to hold his or her breath at the selected state during image acquisition. The image may be a conventional diagnostic image acquired without regard to any special considerations for the therapeutic procedure and indeed acquired before the need for the therapeutic procedure is known.

The image includes at least a portion of the patient's thorax and includes certain features of the patient's anatomy which are readily identifiable in the image with a good degree of precision. These include features of the skeletal system such as the scapula SC, portions of the spine SP and the sternal notch ST. In the conventional manner, the image is provided as computer data defining properties of structures of various locations within the body as, for example, x-ray absorption of individual volume elements or "voxels" in a CAT image or MRI data defining magnetic resonance properties such as proton density, $T_1$ or $T_2$ for individual voxels.

After the image has been acquired, the patient is placed into position in the locating frame of reference defined by external field transducers 40 as, for example, by placing the patient in supine position on the supporting table 41. Reference field transducer 50 is then engaged successively with several of the aforementioned readily defined points on the patient's body as, for example, with each of the scapula, with the sternal notch or with readily identified points on the spine. This is done while the patient remains in position on the table. The table may be provided with apertures or grooves in its surface (not shown) to allow insertion of the reference field transducer 50 into engagement with features of the patient's back. While the reference field transducer is in engagement with each defined point in the patient's anatomy, the external field transducers 40, field transmitting and receiving apparatus 42 and computer 44 are actuated to determine the location of the reference field transducer in the locating frame of reference defined by the external field transducers 40. Thus, the locations of the various defined points in the locating frame of reference are provided to the computer.

An operator can also input the locations of the same defined points in the frame of reference of the image. For example, computer 44 can be actuated to display depictions of the image which include the various identifiable points in the anatomy and the operator can manually adjust a cursor on the image as, for example, by adjusting a knob, trackball or mouse incorporated in input devices 45. When the cursor is aligned with an identifiable point in all dimensions, the operator enters a further signal indicating to the computer that the coordinates of the cursor in the image frame of reference correspond to the coordinates of the particular point in the anatomy. Once the coordinates of the identifiable points in the anatomy have been provided to the computer in the image frame of reference and in the locating frame of reference, the computer can derive a mathematical transformation between the locating frame of reference and the image frame of reference. Techniques for acquiring locations of points in the anatomy and deriving transformations between an image frame of reference and a locating frame of reference are well known and are described in the aforementioned patents and publications. In a variant of such techniques, also described in these patents and publications, fiducial markers incorporating field transducers are mounted on the patient before the imaging procedure, so that the fiducial markers are visible in the image. The positions of the fiducial markers in the locating frame of reference are acquired by actuating the field transducers on the fiducial markers in conjunction with the external field transducers, in the same manner as described above. In other variants, the system acquires a succession of positions in the locating frame of reference while a reference field transducer is moved over a well-defined contour in the patient's anatomy. The computer system uses automatic pattern-matching techniques to find a feature having a contour including a set of locations in the image frame of reference which can be mapped to the set of locations in the locating frame of reference by a rigid-body transformation. Again, various techniques for finding matching points in both frames of reference, and for deriving a transformation between the locating and imaging frames of reference, are well known in the art.

Figure 4:
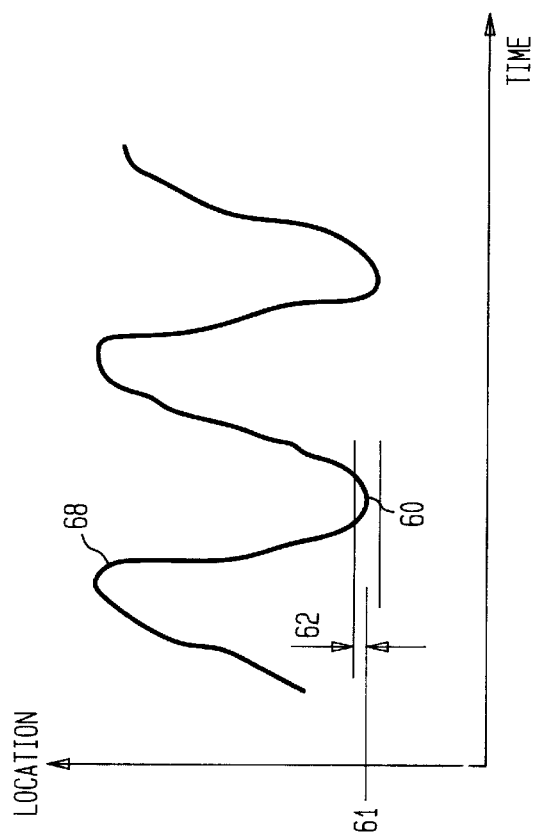
FIG. 4 is a graph of reference point position in operation of the apparatus of FIGS. 1–3.

The reference field transducer 50 is then mounted on a point on the outside of the patient's chest which moves during respiration. For example, the reference field transducer can be taped or sutured in place over one of the patient's ribs. While the patient remains in position on Table 41, the patient breathes normally and hence reference field transducer 50 moves cyclically in a motion corresponding to the various phases of the respiratory cycle. Thus, the location of reference field transducer 50 varies with time. The computer, in cooperation with the field transmitting and receiving unit and external field transducers 40 continually monitors the position of reference field transducer 50. The computer tracks the position of the reference field transducer over time and generates a plot of the reference field transducer position in a selected direction versus time. The plot is depicted in graphical form in FIG. 4 for ease of understanding. In practice, the plot consists of a series of numbers denoting the location of the reference transducer along the selected axis at various times. The axis selected for tracking may be a vertical axis (towards and away from the table in FIG. 1) and hence towards and away from the patient's back; a horizontal axis transverse to the longitudinal (head-to-toe) axis of the patient or an axis at an arbitrary angle between the vertical and the horizontal.

The computer selects successive extreme positions in the plot. For example, where the location represented by the plot is location in a vertical axis corresponding to movement towards and away from the patient's back, the computer may be actuated to select successive minima 60 of such location, i.e., the points where the reference field transducer is closest to the patient's back. Alternatively, where the location represented by the plot is horizontal location, the computer may be actuated to select minima in the plot corresponding to locations where the reference field transducer is closest the central axis of the patient. These minima can be found by conventional computer-programming techniques for selecting local minimum values in a sequence of numbers. Numerical techniques of this nature are well known in the programming arts and are available in many standard mathematical software packages. The minima represent the minimum inspiration point in the patient's respiratory cycle as discussed above.

The value of the location at successive minima may not be exactly the same. However, for a patient breathing normally, all of the minima will have values close to one another. Thus, the computer calculates a mean value 61 representing the mean location of several successive minima. The system then applies a preselected tolerance or maximum deviation 62. Whenever the location of reference field transducer 50 deviates from the mean value 61 by less than a predetermined tolerance 62, the system treats the patient as being at the minimum inspiration point of the respiratory cycle. Thus, by monitoring the respiratory cycle, the system establishes a particular respiratory state corresponding to an extreme of the movement of the reference transducer encountered in normal respiration.

The physician advances the distal end 26 of the probe into the respiratory system of the patient in the conventional manner. Typically, the distal end of the probe is advanced through an airway A as, for example, through the larynx and trachea into the bronchi. Computer 44, field transmit and receive unit 42 and external field transducers 40 cooperate with probe field transducer 30 to determine the position of the probe field transducer and hence the position of the probe distal end 26 in the locating frame of reference defined by the external field transducers 40, and cooperate with reference transducer 50 to determine its position. When the position of the reference transducer is within the predetermined tolerance 62 of the mean minimum inspiration location 61, the computer captures the location of the probe field transducer and probe distal end in the locating frame of reference defined by the external field transducers. Thus, the computer captures the location of the probe distal end when the patient is at the minimum inspiratory state.

Figure 2:
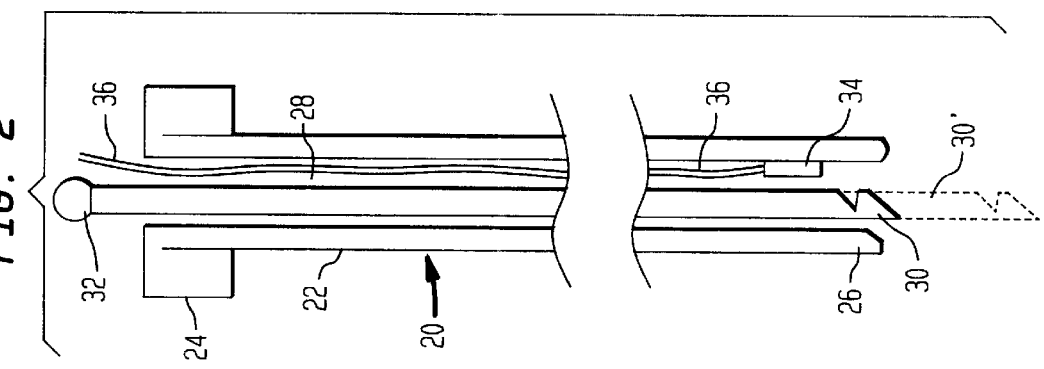
FIG. 2 is a diagrammatic sectional view depicting further elements of the apparatus of FIG. 1.

The computer transforms the location of the probe distal end into the frame of reference of the image and prepares a composite display including at least a portion of the image and a representation of the probe superposed on the image. For example, as shown in FIG. 1, the displayed image on cathode ray tube 46 includes a depiction A' of the portion of the airway together with a representation 26' of the probe distal end. The image also includes a depiction T of the target tissue, in this case a lesion outside of the airway but adjacent thereto. Preferably, the image displayed is a perspective view, so that the physician can readily perceive the spatial relationships between the distal end of the probe and the target tissue. The system may also generate a line or arrow 66 on the displayed image showing the trajectory from the probe distal tip to the target. The physician can use the information shown in the displayed image to bring the probe distal end into engagement with the target. For example, the physician can bring the distal end of the probe body 22 into engagement with the airway adjacent the target and can advance the biopsy needle 30 to its extended position 30' (FIG. 2) and thus pierce the airway wall and engage the target.

Because the location of the probe distal end is captured only when the patient is in the same respiratory state as used in image acquisition, the acquired position of the probe distal end, transformed into the frame of reference of the image accurately represents the relative position of the probe distal end and the surrounding tissues. The patient continues to breathe while the probe is advanced into the airway. A new probe position is acquired on each respiratory cycle when the patient reaches the minimum inhalation state. Each time a new probe position is acquired, the display shown on CRT screen 46 is revised to conform with the new probe position. Thus, the physician can monitor the progress of the probe distal end towards the target tissue. The physician can accurately align the probe with the target tissue.

The procedure discussed above can be varied in many ways. For example, the computer can be adjusted to find the mean location for the maximum inhalation 68 of the patient's respiratory cycle, and the image may be acquired at a similar maximum inhalation state. In a further variant, the computer can select an arbitrary axis for plotting motion of the reference transducer so that the axis is aligned with the principal direction of motion of the reference field transducer during respiration. For example, the computer can first track the location of the reference field transducer using a horizontal, vertical or other preset axis to find maxima and minima in the location on that axis. The computer can then compute the average time between successive maxima or successive minima. That time corresponds to the period of the respiratory cycle. The computer can then test various pairs of locations, each including one point delayed in time by one full period from another point.

The computer can then calculate the distance in three dimensional space between each pair of points. The pair of points which has the largest distance lie along the principal direction of movement of the reference field transducer during the respiratory cycle. The computer can then plot location along this direction versus time.

The image may be acquired when the patient is at an abnormal respiratory state such as a maximum forced exhalation obtained by deliberately forcing exhalation with maximum voluntary effort, or a maximum forced inhalation obtained by deliberately forcing maximum inhalation with a maximum voluntary effort. In this case, the state used during image acquisition will not recur during a normal respiratory cycle. Instead, the patient is instructed to repeat the state while the system monitors the location of reference field transducer 50. After the patient repeats the state in one or more trials, the system records the location of the reference transducer at this state, or the mean location obtained in several trials. While the physician is advancing the probe into the respiratory system, the patient is instructed periodically to repeat the same state. The system acquires the image when the patient is holding his or her breath at the desired respiratory state. An arbitrary respiratory state such as a state midway between the maximum and minimum inhalation in a normal respiratory cycle can also be used. However, the patient typically will not be able to reproduce such an arbitrary state accurately. In methods according to a further embodiment of the invention, the system can provide guidance to the patient and the physician to aid in duplicating an arbitrary respiratory state. Thus, if the reference transducer 50 is mounted on the patient before the imaging procedure, and if the reference field transducer is visible in the image, the position of the field transducer relative to the identifiable points on the body, such as the scapular spine or sternum will vary with the respiratory state of the patient. For example, if the reference field transducer is mounted to the ribs, the field transducer will move outwardly, away from the central axis of the body as the patient inhales. When the patient is placed on table 41, in proximity to the external field transducers, the system can track the location of the reference field transducer in the manner discussed above. The position of the reference field transducer can be transformed into the frame of reference of the image. If the patient is in the same respiratory state as was used in image capture, the position of the reference field transducer in the image frame of reference will overlie the depiction of the reference field transducer in the image. In a further variant, two or more reference transducers may be attached to the patient at locations which move towards or away from one another during respiration. The system can track the distance between the reference transducers as a measure of respiratory state.

The physician can use the information as to the respiratory state provided by the reference transducer or transducers to provide feedback to the patient, as, for example, by instructing the patient to inhale or exhale slightly to better match the respiratory state used during image capture. Alternatively, a mechanical respirator can be controlled automatically to achieve superposition between the position of the reference field transducer as determined by the field transmitting and receiving apparatus and the position depicted in the image. Thus, the respirator may be arranged to provide substantially normal breathing followed by periods of forced breath holding and inflation of the lungs to the extent necessary to match the position captured in the image.

In the procedures discussed above, the probe is advanced through the airway. However, the same advantages can be obtained in procedures where the probe is advanced through the skin or through the intestinal track to other organs affected by motion due to respiration.

As these and other variation and combinations of the features discussed above can be utilized without departing from the present invention, the foregoing description of the preferred embodiment should be taken by way of illustration rather than by way of limitation of the invention defined by the claims.

What is claimed is:

1. A method of performing a medical procedure on the respiratory system of a patient comprising the steps of:

(a) acquiring an image of the patient in an image frame of reference while the patient is at a selected respiratory state;

(b) advancing a probe into the respiratory system of the patient (c) during said advancing step, determining the disposition of the probe in a locating frame of reference while the patient is at said respiratory state by transmitting one or more non-ionizing fields to or from at least one probe field transducer on said probe and detecting one or more properties of the transmitted fields;

(d) transforming at least one of the image and disposition of the probe in said locating frame of reference so as to place the image and the disposition of the probe in a common frame of reference;

(e) displaying said image of the patient with a representation of the probe superposed thereon at a location corresponding to the disposition of the probe in the common frame of reference;

(f) detecting when the patient is in said respiratory state by monitoring the position of a reference point on the patient which moves in the respiratory cycle, wherein said selected respiratory state is a stage of the patient's normal respiratory cycle; and (g) establishing a position of said reference point corresponding to said selected stage of the respiratory cycle by monitoring the position of said reference point over a plurality of cycles and finding an extreme position of the reference point which recurs in each cycle based on such monitoring.

2. A method as claimed in claim 1 wherein said extreme position corresponds to minimum inspiration.

3. A method as claimed in claim 1 wherein said step of detecting when the patient is in said selected stage includes the step of determining whether the position of the reference point matches the extreme position found in said establishing step to within a preselected tolerance.

\* \* \* \* \*